United States Patent
Kuster et al.

(10) Patent No.: US 8,641,740 B2
(45) Date of Patent: Feb. 4, 2014

(54) BONE ANCHORING DEVICE FOR THE OPERATIVE REPAIR OF FRACTURES

(75) Inventors: Markus Kuster, St. Gallen (CH);
Jordan Velikov, Gockhausen (CH);
Miodrag Garic, Winterthur (CH);
Thomas Teschke, Zürich (CH)

(73) Assignee: Zimmer, GmbH, Winterthur (CH)

( * ) Notice: Subject to any disclaimer, the term of this patent is extended or adjusted under 35 U.S.C. 154(b) by 178 days.

(21) Appl. No.: 12/680,120

(22) PCT Filed: Sep. 26, 2008

(86) PCT No.: PCT/EP2008/062974
§ 371 (c)(1),
(2), (4) Date: Apr. 27, 2010

(87) PCT Pub. No.: WO2009/043827
PCT Pub. Date: Apr. 9, 2009

(65) Prior Publication Data
US 2010/0211112 A1   Aug. 19, 2010

(30) Foreign Application Priority Data

Sep. 26, 2007  (EP) ..................................... 07117227
Dec. 19, 2007  (CH) ..................................... 1992/07

(51) Int. Cl.
*A61B 17/80* (2006.01)
(52) U.S. Cl.
USPC ........................................................ 606/280
(58) Field of Classification Search
USPC .......... 606/280, 286–296, 319–320, 902–906
See application file for complete search history.

(56) References Cited

U.S. PATENT DOCUMENTS 5,234,431 A  8/1993  Keller
5,269,784 A  12/1993  Mast
(Continued)

FOREIGN PATENT DOCUMENTS

EP  0507162 A1  10/1992
EP  0968685 A2  1/2000
(Continued)

OTHER PUBLICATIONS

The published International Search Report of parent application No. PCT/EP2008/062974 published Apr. 9, 2009.
(Continued)

*Primary Examiner* — Sameh Boles
(74) *Attorney, Agent, or Firm* — Schwegman, Lundberg & Woessner, P.A.

(57) ABSTRACT

The invention relates to a bone anchoring device for the operative repair of fractures, comprising a fracture fixation plate which has at least one opening and at least one anchoring element for the fastening of the fracture fixation plate on the bone, wherein the anchoring element has a shaft and a head, and wherein at least one part of the shaft can be guided through the opening while the head can be fixed in the opening, and wherein the shaft is produced in at least two parts with a first part on which the head is arranged and with a second part provided for the anchoring in the bone, wherein the first part and the second part of the shaft are guided such that they move toward each other along an axis when the bone anchoring device is in the state of being fixed to the bone.

16 Claims, 6 Drawing Sheets

(56) References Cited

U.S. PATENT DOCUMENTS

2005/0182406 A1* 8/2005 Orbay et al. .................. 606/69
2005/0234457 A1* 10/2005 James et al. .................. 606/69

FOREIGN PATENT DOCUMENTS

| EP | 1495733 | A2 | 1/2005 |
| FR | 2899787 | A1 | 10/2007 |
| WO | WO01/91660 | A1 | 12/2001 |
| WO | WO03/101321 | A1 | 12/2003 |
| WO | WO2004/075766 | A1 | 9/2004 |

OTHER PUBLICATIONS

"International Application Serial No. PCT/EP2008/062974, International Preliminary Report on Patentability mailed Apr. 27, 2010", 7 pgs.

"International Application Serial No. PCT/EP2008/062974, Written Opinion mailed Jan. 15, 2009", 6 pgs.

\* cited by examiner

BONE ANCHORING DEVICE FOR THE OPERATIVE REPAIR OF FRACTURES

This application is a U.S. National Phase Patent Application based on International Application Serial No. PCT/EP2008/062974 filed Sep. 26, 2008, the disclosure of which is hereby explicitly incorporated by reference herein.

TECHNICAL AREA

The invention relates to a bone fixing apparatus of the kind described in claim 1.

PRIOR ART

For the treatment of a bone fracture such as a fracture of the proximal humerus, the fracture is fixed by means of pins, screws, wires or plates after alignment of the individual bone fragments in their correct positions (repositioning). A plate can in particular be used for the fixing which is fastened to the individual bone fragments by means of screws. In this kind of treatment, a compressive effect is achieved such that the individual bone fragments are held in a fixed position with respect to one another and are pressed toward one another by the plate and by the screws. To reduce the risk of a periosteal circulation disorder, the plate used for the fixing is, for example, fixed at a spacing, i.e. without contact to the surface of the bone.

An osteosynthetic plate is, for example, offered by the applicant for the care of fractures of the proximal humerus under the name NCB (Non-Contact Bridging) which permits a polyaxial screw arrangement with subsequent securing of the screws for higher stability, particularly in porotic bones. The screws can be fixed in the plate at varying angles of up to approximately 30° for the optimum care of the fracture at a stable angle. After the suitable positioning of a screw, it is clamped tightly in the plate to fix the fracture fragments in the correct position with respect to one another. In the secured state, the osteosynthetic plate therefore serves as an internal fixation for the fracture of the humerus without contact of the plate to the bone surface. The risk of a periosteal circulation disorder is hereby reduced.

REPRESENTATION OF THE INVENTION

A bone fixing apparatus for the surgical care of fractures is now proposed here in which the risk of injury to a joint is reduced on use in a region close to the joint and/or in which the compressive effect is reduced.

A bone fixing apparatus for the surgical care of fractures is provided. The bone fixing apparatus includes a fracture fixing plate, with the plate having at least one opening. In an embodiment, the plate in particular has a first side formed for arrangement remote from the bone and a second side formed for arrangement toward the bone, with at least one opening being arranged in the plate which leads from the first side to the second side. The side of the plate formed for arrangement toward the bone is in particular characterized in that its shape is adapted to this purpose. The geometry and contour of this side is designed such that the plate substantially has a typical negative mold of the bone at which it is provided for arrangement. That is, this mold is not adapted from patient to patient, but is rather adapted to a typical "average" bone, with a plate usually being available in a plurality of sizes for a bone. The bone fixing apparatus furthermore includes at least one anchorage element for the fastening of the fracture fixing plate to the bone, with the anchorage element having a shaft and a head. The head is preferably arranged at an end of the anchorage element at the manipulation side. At least a part of the shaft can be passed through the opening, whereas the head can be fixed in the opening. The shaft is made in at least two parts, in particular in two parts, with a first part at which the head is arranged and with a second part provided for the anchorage in the bone. The first part and the second part are guided displaceably to one another along an axis and are in particular guided freely displaceable in the state in which the bone fixing apparatus is fixed to the bone. In accordance with an embodiment, the first part and the second part can slide with respect to one another, can in particular slide freely, in a linearly guided manner in the direction of the axis. In accordance with an embodiment, the shaft can in particular be telescoped out, moved out and/or extended.

A major idea of embodiments of the invention is to use a fracture fixing plate for the fixing of bone fragments with a bone fixing apparatus, said fixing plate being fixed to the bone by means of at least one anchorage element or of a sliding anchorage, in particular formed from a sleeve and a pin-shaped element or fastening element slidingly supported therein, with the first part and the second part of the shaft of the respective anchorage elements being guided displaceably to one another, in particular not only on the assembly, but rather also in the state fixed to the bone.

The anchorage element can, for example, be used to hold two bone fragments of a condyle head fracture against one another whose fracture line extends transversely to the axis of the anchorage element. Provided that in such a case the one bone fragment, which is in particular in contact with the associated joint cavity, moves in the direction of the other bone fragment, for example by being sintered together, in particular during the healing process, a piercing of the anchorage element into the joint can be avoided. This results from the fact that the tip of the anchorage element, which is anchored in the one bone fragment can migrate along with the one bone fragment due to the displaceability of the two shaft parts toward one another. The anchorage element can also advantageously be used with fractures of bones of children or juveniles having a growth line extending transversely to the axis of the anchorage element. Bone growth is hindered as little as possible by the displaceability of the two shaft parts toward one another.

The compressive effect of the bone fixing apparatus can be effectively reduced by the use of such an anchorage element since substantially only transverse forces are transmitted through the anchorage element, but not forces acting along the anchorage element.

Possible injury to the joint surface in particular in the region close to the joint can thereby be prevented due to the reduced compressive effect since the anchorage element can be displaced in the direction of the axis, in particular of its longitudinal axis, on a load of the joint, and thus with respect to the plate and thus a piercing of the anchorage element into the joint can be prevented under certain circumstances.

Any kind of stabilization or anchorage element is to be understood under an anchorage element within the framework of the present invention which can be used with a bone fixing apparatus, that is also in particular sliding bars or sliding bolts in combination with sleeves in which they are slidingly supported, with the sleeves being able to be anchored in the bone.

In accordance with an embodiment, the anchorage element includes a sleeve having an inner guide region and an element, in particular of pin-shape, which is received therein, having an outer guide region, said regions having a constant cross-section in each case in the direction of the axis such that the outer guide region can slide in a linearly guided manner in the direction of the axis in the inner guide region. The cross-sections of the inner guide region and of the outer guide region are matched to one another to enable a sliding into one another and are circular in an embodiment.

In accordance with an embodiment, a bone fixing apparatus is provided for the surgical care of fractures which includes the following:

- at least one sleeve which is designed for the sliding reception of a pin-shaped fastening element such that the pin-shaped fastening element can slide along its longitudinal axis in the sleeve;
- at least one pin-shaped fastening element which has an anchorage section for the fixing of the element and a sliding section for the sliding reception in the sleeve; and
- a fracture fixing plate which has at least one opening for the support and/or fixing of the sliding anchorage formed from a sleeve and a pin-shaped fastening element slidingly supported therein at a specific angle to the fracture fixing plate.

In such a bone fixing apparatus, the sliding anchorage can slide along its longitudinal axis in the sleeve so that, on a loading of the fracture, in particular of the proximal humerus, effected by a muscular contraction, for example, a piercing of the bone by the tip of the sliding anchorage can be efficiently prevented.

In accordance with an embodiment, the element, in particular of pin shape, is formed for the anchorage in the bone and the sleeve for the fixing in the at least one opening of the fracture fixing plate. The pin-shaped element or fastening element can in particular be a bone screw and the aforesaid anchorage element of the bone screw can be designed for the fixing of the screw in a bone, can, for example, have a thread for screwing into the spongiosa of a bone, and the at least one opening of the fracture fixing plate can be designed for the support and/or fixing of the sleeve at a specific angle to the fracture fixing plate. In this embodiment, the sleeve is therefore supported and/or fixed in the fracture fixing plate, whereas the bone screw is slidingly supported in the sleeve as a pin-shaped element and is anchored in the bone.

In accordance with another embodiment, the sleeve is designed for the anchorage in the bone and the element, in particular of pin shape, is designed for the fixing in the at least one opening of the fracture fixing plate. The pin-shaped element or fastening element can in particular be a sliding pin and the aforesaid anchorage section of the sliding pine can be designed for the fixing of the sliding pin in the at least one opening of the fracture fixing plate and the at least one opening of the fracture fixing plate can be designed for the support and/or fixing of the sliding plate at a specific angle to the fracture fixing plate. The sleeve is here therefore anchored, for example screwed, in the bone and the sliding pin is slidingly supported as a pin-shaped element in the sleeve anchored in the bone and fixed in the opening of the fracture fixing apparatus.

In accordance with an embodiment, a bone fixing apparatus with a fracture fixing plate having at least two openings and with at least two anchorage elements is provided, with at least one anchorage element being designed such that the pin-shaped element is designed for the anchorage in the bone and the sleeve for the fixing in the at least one opening of the fracture fixing plate, and with at least one other anchorage element being designed such that the sleeve is designed for the anchorage in the bone and the element, in particular of pin shape, is designed for the fixing in the at least one opening of the fracture fixing plate. In further embodiments, at least one sliding length-variable anchorage element and one length-invariable anchorage plate, as described, is arranged in the plate or provided for arrangement in the plate.

The sleeve or the sliding pin can have the head or head section for support in the opening of the fracture fixing plate. The head can, for example, serve the purpose of preventing a sliding of the sleeve or of the sliding pin through the opening in the fracture fixing plate, for example when the sleeve or the sliding pin is introduced through the opening of the fracture fixing plate during an operation.

In accordance with an embodiment, the total anchorage element can be inserted with only access from a side of the plate remote from the bone and/or the complete shaft of the anchorage element, but not the head of the anchorage element, can be passed through the opening. The anchorage element can in particular be inserted through the opening of the plate into the bone. First the plate can be introduced and the anchorage element can only then be introduced into the body of a patient. An operation can hereby be carried out minimally invasively.

In accordance with an embodiment, the dimensions of the head and of the opening are matched to one another such that the head cannot be passed through the opening. The head can have a support surface with which the head lies at the margin of the opening in the state in which the bone fixing apparatus is fixed to the bone. The headless part of the shaft can be passed through the opening or cannot be passed through the opening.

In particular the head or head section and the opening can furthermore be designed such that the angular position of the anchorage element, in particular of the sleeve or of the sliding pin, to the fracture fixing plate can be adjusted within a preset angular range before a fixing. This enables a polyaxial setting of the position of the anchorage element and thus a direct alignment of the anchorage element so that a fracture can first be brought into the correct position and the anchorage elements can subsequently be aligned such that conditions which are as good as possible can be achieved for a healing of the fracture.

In accordance with an embodiment, means are provided to connect the head of the anchorage element to the plate, in particular with respect to the axial position and/or the angular position of the anchorage element or of the part of the anchorage element at which the head is arranged.

In accordance with an embodiment, the plate has a recess in the region of the opening for the part or also full reception of the head of the anchorage element. The recess is in particular arranged at the side of the plate provided remote from the bone.

The head or head section can have an external thread and the opening or a recess of the opening can have an internal thread into which the head section can be screwed. The anchorage element, in particular the sleeve or the sliding pin, can hereby be directly anchored in the fracture fixing plate by screwing into the fracture fixing plate, whereby a particularly stable connection of plate and anchorage element is achieved. Such a connection is unidirectional since the alignment of the anchorage element is preset and a movement, for example, of the bone screw or of the sliding pin in the sleeve, is thus only possible in the longitudinal direction.

A blocking element can be provided to block the head within the opening or a recess of the opening. The opening or the recess can have an internal thread and a closure element, in particular a closure screw or a closure ring, can be provided as a blocking element having an external thread for the blocking of the head by screwing into the opening or the recess. The closure screw above all serves to anchor the anchoring element fixedly in the fracture fixing plate at a specific angular position, in particular determined in accordance with an alignment of the anchorage element, in particular to avoid a displacement of the angular position of the anchorage element where possible during the operation.

In accordance with an embodiment, the plate has a concave support surface, that is a support surface arched into the plate, in the region of the opening or of the recess of the opening facing the side of the plate facing the bone and/or the head is designed spherically at the end facing the shaft such that the anchorage element is variable with respect to its angular position toward the plate before a fixing.

The fracture fixing plate can be designed for the care of a joint fracture, in particular of a fracture of the proximal humerus, and/or for the arrangement in the epiphyseal and/or metaphyseal region of a bone, in particular of the proximal humerus, and can in particular have a plurality of openings for the support and fixing of anchorage elements, in particular of sleeves or sliding pins, which are arranged in a section of the fracture fixing plate provided for the care of the fracture region close to the joint. The use of the anchorage elements, in particular of the slidingly supported pin-shaped elements or fastening elements such as bone screws or sliding pins, in the region of a fracture close to a joint can efficiently counteract an injury to the joint surface. On a high mechanical load of the joint surface, the pin-shaped element or fastening element can, for example, be displaced in the sleeve, whereby a piercing of a screw tip or sleeve tip into the joint can largely be avoided. A rotation of bone fragments can furthermore be prevented by the arrangement of at least two anchorage elements, in particular slidingly supported pin-shaped elements or fastening elements, in the region close to the joint since the fracture can be fixed in a stable manner except for a movement in the direction of the axis, in particular in the longitudinal direction of the pin-shaped elements.

The bone fixing apparatus can furthermore be designed such that the fracture fixing plate can substantially be fixed without contact to the bone surface, in particular by fixing the head of the respective anchorage element to the plate. The risk of a periosteal circulation disorder at the bone surface of the fracture can thereby be reduced.

The pin-shaped element or fastening element can be cannulated, in particular to receive a guide wire for the positioning of the element. The guide wire can serve, for example, for the predrilling into the bone or for the support in the alignment of a sleeve and of the pin-shaped element.

Another embodiment relates to an anchorage element for the fastening of a fracture fixing plate to the bone, including a shaft as well as a head, with the shaft being made in at least two parts, having a first part at which the head is arranged and having a second part provided for the anchorage in the bone, with the first part and the second part being guided displaceably with respect to one another along an axis in the state in which the bone fixing plate is fixed to the bone.

A further embodiment relates to a method for the surgical care of a fracture using a bone fixing apparatus, in particular as described above, in particular a minimally invasive surgical procedure, wherein a fracture fixing plate is introduced into the body of a patient at the site of the fracture;
the fracture is reduced with the aid of the introduced fracture fixing plate;
bores for the reception of anchorage elements, in particular of sleeves or pin-shaped elements such as bone screws, are introduced into at least some of the bone fragments of the fracture;
the anchorage elements or parts thereof, in particular the sleeves and/or the pin-shaped elements such as bone screws or sliding pins, are introduced into the bores; and
the anchorage elements are fixed at a stable angle in the fracture fixing plate.

The anchorage elements or the parts thereof can be introduced into the bores before or after a final introduction of the fracture fixing plate into the body of the patient.

For example, such a surgical procedure can be used for the conservative care of a fracture of the proximal humerus.

Further aspects of the invention form the subject of the dependent claims.

The features of the aforesaid embodiments of the invention can naturally each be combined with one another to form specific embodiments.

BRIEF DESCRIPTION OF THE DRAWING

The invention will be explained in more detail in the following with reference to embodiments shown in the drawing. There are shown in detail FIG. 1 as an embodiment of a bone fixing apparatus, a humerus plate in which three anchorage elements are arranged in the proximal section of the plate.

The following description of the embodiments and the drawings serve for the better understanding of the invention and should not be used to restrict the invention characterized in the claims.

WAYS OF PERFORMING THE INVENTION

Embodiments of the invention will be described in the following for the example of a bone fixing apparatus for the surgical care of a humerus fracture in particular of a fracture of the proximal humerus, although the invention is not restricted to such an application, but can rather be used for any kind of fracture care. The bone fixing apparatus can in particular also be used for fracture fixing at other bones than at the humerus, in particular also at the tibia or at the femur. The invention, however, in particular shows considerable advantages with respect to conventional fixing apparatus, in particular in the region close to the joint, due to the reduced compressive effect with respect to the load capability of joints during the healing process and with respect to the reduction of the risk of joint injuries, in particular due to load and compression increased thereby.

In the following, the term "sliding screw" is used as a designation for the combination of a sleeve and of a bone screw slidingly guided therein along its longitudinal axis or of a sliding pin slidingly guided therein along its longitudinal axis in the sense of a pin-shaped element or fastening element. The sliding screw serves here in the sense of the invention as an anchorage element or as a sliding anchorage of the humerus plate to the bone.

The humerus plates which are described in the following as examples for fracture fixing plates which substantially do not have any contact to the bone surface are based on the principle of plate fixing at a stable angle in which sliding screws supported in the humerus plate are anchored at a stable angle. Two different kinds of fixing of the sliding screws are available for this purpose:

1. Unidirectional or uniaxial fixing: the angular position of a sliding screw is not freely selectable since it is passed through the opening in the plate, through which the sleeve of the sliding screw or the pin-shaped element is guided and the fixing of the sliding screw in the plate is preset.
2. Polyaxial or polydirectional fixing: the sliding screw can be fixed in the opening of the plate at varying angular positions, typically at angles up to approximately 30°. The fixing is therefore not fixed in advance, but can rather take place, for example, by clamping of the sleeve of the sliding screw or of the pin-shaped element in the opening. An adaptation of the position of the sliding screw to the anatomy of the bone can thereby be achieved.

In both fixing cases, the humerus plate is adapted to an average anatomy of the humerus. More generally, the shape of the respective bone fixing plate is adapted to the shape of the respective bone or bone type to be fixed.

Figure 1:
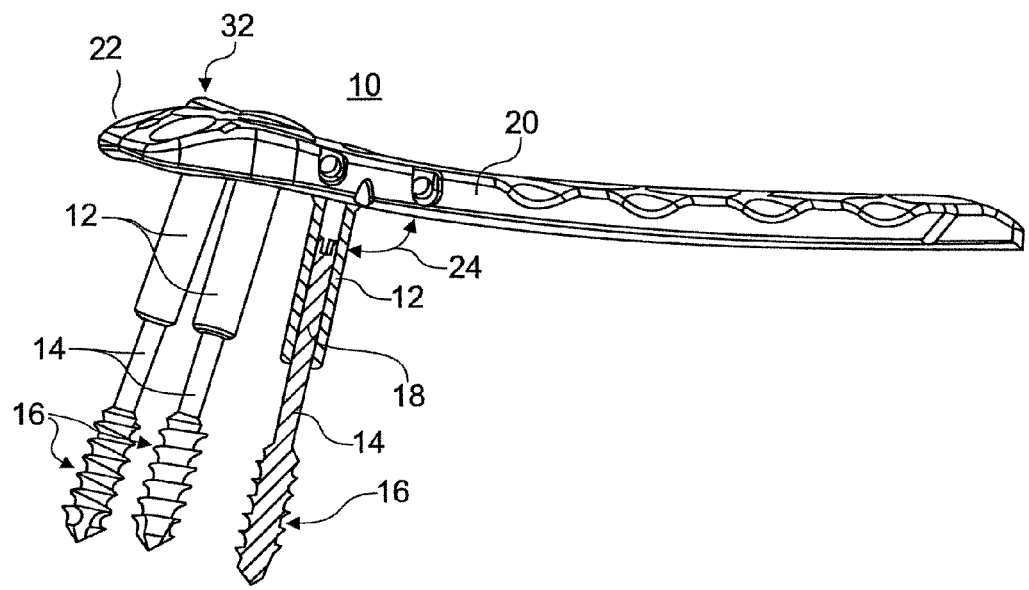

The bone fixing apparatus 10 shown in FIG. 1 includes a humerus plate 20. The humerus plate 20 having a first side directed upwardly in FIG. 1 and remote from a bone (not shown) and having a second side directed downwardly in FIG. 1 and facing the bone is provided with three anchorage elements or sliding screws introduced into and fixed to the plate 20. The side of the plate 20 remote from the bone is that side of the plate 20 on which the head of screw is located in the state in which the bone fixing apparatus is fixed to the bone. The sliding screws each include a sleeve 12 and a bone screw 14 slidingly guided therein. The sleeve 12 and the bone screw 14 form a two-part shaft of the sliding screw. The sleeve 12 and the bone screw 14 are also guided freely displaceably with respect to one another along their common longitudinal axis in the state in which the bone fixing apparatus is fixed to the bone, i.e. in particular in the intended use or state of the bone fixing apparatus. The sliding screw can therefore be pulled out telescopically. The relative position of the two parts with respect to one another is unchangeable or fixed transversely to the axis.

The sleeves 12 are supported in the humerus plate 20. For this purpose, the sleeves 12 are passed through openings 22 in the plate 20 which extend from the first side of the plate 20 through the plate 20 to the second side of the plate 20 so that they each project into a bore (not shown) introduced into the bone. Each of the sleeves 12 can be fixed at a specific angle 24 to the humerus plate 20 and can thus be ideally adapted to the anatomy of the bone and of the fracture to be fixed. The humerus plate 20 has a section 32 which is close to the joint and which is formed for the care of the fracture region of the humerus close to the joint, i.e. is shaped correspondingly anatomically. The three sliding screws are arranged in this section 32 and can thus effectively prevent a rotation of bone fragments. A fracture can thus be stabilized except for a movement in the longitudinal direction of the sliding screw.

Each bone screw 14 has a threaded section 16 as an anchorage section which is screwed into the bone for the fixing of the fracture. Each bone screw 14 furthermore has a sliding section 18 having an outer guide region in the form of a threadless screw section which adjoins the threaded section 16 and is located at least party in a sleeve 12 fixed in the humerus plate and having an inner guide region. The sliding section 18 can move freely slidingly in the sleeve 12 in a linearly guided manner in the direction of the longitudinal axis of the bone screw 14 anchored in the bone, whereby substantially no longitudinal forces which act on the bone screw 14 and which occur, for example, on a loading of the bone, are transferred to the bone fixing apparatus. The outer guide region of the sliding section 18 and the inner guide section of the sleeve 12 each have a constant cross-section in the direction of their longitudinal axis, i.e. they are each cylindrical. The outer guide region and the inner guide region ensure a guidance of sleeve 12 and pin-shaped element 14 transversely to the longitudinal axis.

Figure 2:
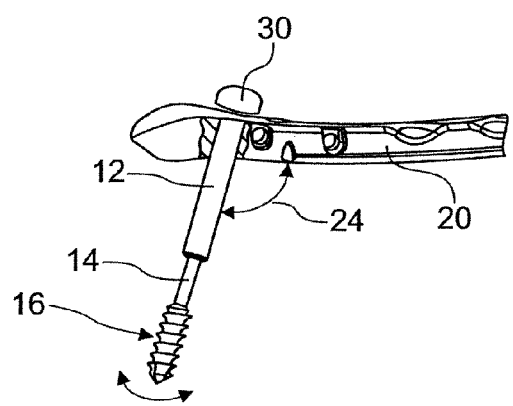
FIG. 2 as a further embodiment of a bone fixing apparatus, a humerus plate, partly in section, with a polyaxially alignable anchorage element.
Figure 13:
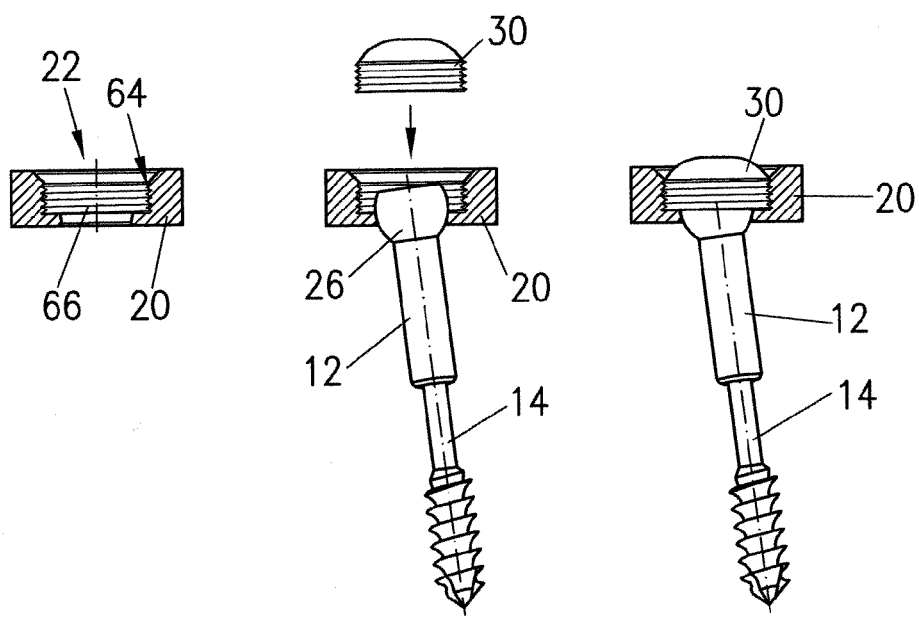
FIG. 13 an embodiment of a polyaxially alignable anchorage element with a closure screw.

FIG. 2 shows a sliding screw polyaxially fixable in the humerus plate 20 and including a sleeve 12 and a bone screw 14. The angle 24 between the sliding screw and the humerus plate 20 can be varied up to approximately 30° by the polyaxial fixing. This allows a direct alignment of every individual sleeve 12 and bone screw 14, in particular to the anatomy and fracture of the bone. The fixing of the sleeve 12 in the humerus plate 20 takes place in a force-transmitting manner by a closure screw 30 which is screwed into the opening 22 of the humerus plate 20 and clamps the sleeve 12 in the intended angular position, as is shown in FIG. 13, so that a subsequent change of the angular position is prevented. A surgeon can thereby bring a fracture into the correct position and hold it fixed, whereby ideal conditions for the healing of the fracture are achieved.

In FIG. 13, a humerus plate 20 is shown having a polyaxial sliding screw in the region of an opening 22, with the plate 20 being shown in three different configurations, namely alone, with an inserted sliding screw and with a fixed sliding screw. The opening 22 of the humerus plate 20 has a recess 66, in which a head 26 of the sliding screw is completely received, on the side of the humerus plate 20 remote from the bone. The head 26 is arranged at an end of the sliding screw at the manipulation side; in the embodiment in accordance with FIG. 13 at an end of the sleeve 12 at the manipulation side. The head 26 adjoins the shaft of the sliding screw. The plate has a concave support surface at a region of the opening 22 or of the recess 66 facing the side facing the bone. The head 26 is designed spherically at least the end facing the shaft to form a counter shape to the concave support surface of the opening 22. The angular position of the sliding screw with respect to the humerus plate 20 is therefore generally variable. The sliding screw is completely, with the exception of the head 26, guidable through the opening 22.

The opening 22, in particular the recess 66, furthermore has an internal thread 64 on the side of the humerus plate remote from the bone. The closure screw 30 which has an external thread corresponding to the internal thread 64 can be screwed into the internal thread 64 to press the head 26 of the sliding screw toward the support surface of the recess 66 in the respective selected angular position of the sliding screw. The head 26 is thereby blocked within the opening 22 such that the angular position of the sliding screw with respect to the humerus plate 20 is fixed. The head 26 of the sliding screw is hereby connected, in particular fixedly or rigidly, for example by force transmission or form fitting, to the humerus plate 20.

Figure 14:
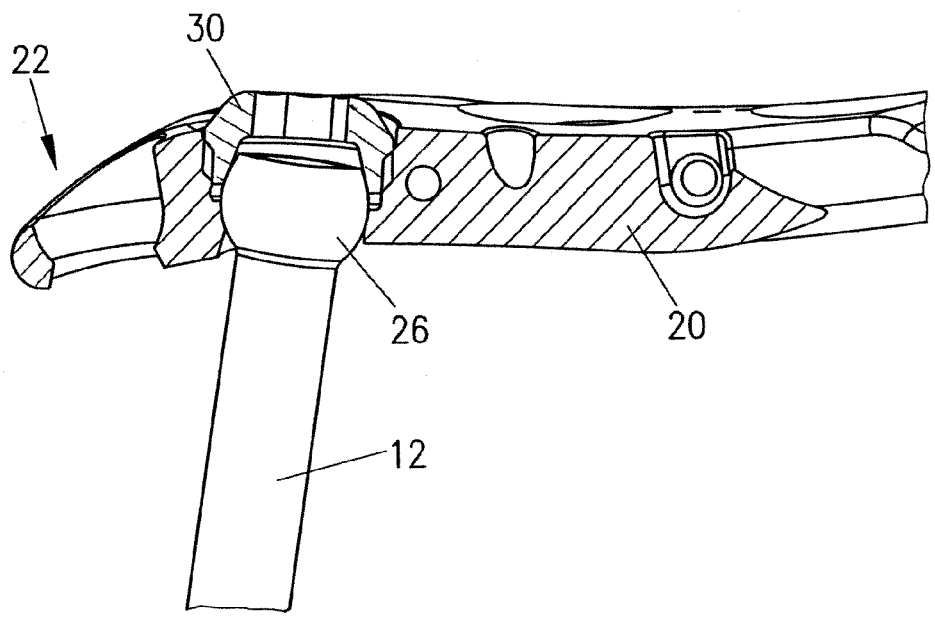
FIG. 14 a further embodiment of a polyaxially alignable anchorage elements with a closure screw.

A further embodiment of a bone fixing apparatus which substantially corresponds to the embodiment shown in FIG. 13 is shown in FIG. 14, with the representation of threads being omitted for reasons of simplicity.

Figure 3:
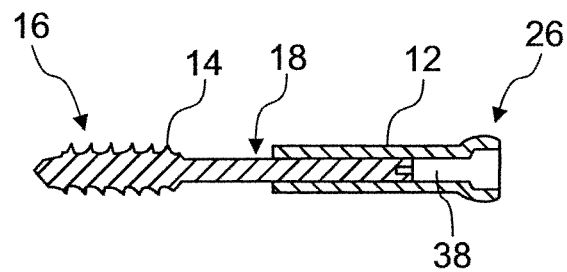
FIG. 3 the anchorage element inserted into the humerus plate of FIG. 2 in a longitudinal section.
Figure 6:
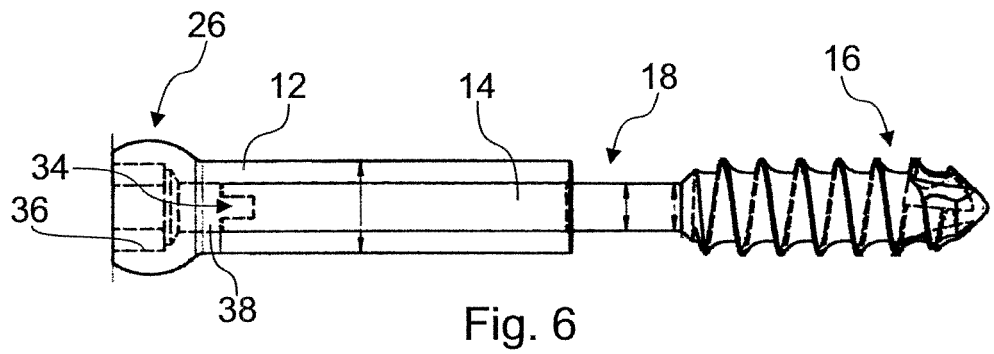
FIG. 6 a design drawing of a polyaxially alignable anchorage element for a humerus plate.

The sleeve 12 used and the bone screw 14 slidingly guided therein are shown in FIG. 3 and in FIG. 6 with reference to a design drawing in a longitudinal section. The head section 26 of the sleeve 12 is, as already explained above, formed similar to a hemisphere for support in the complementary formed opening 22 in the humerus plate 20. Due to the shape of the head section 26 and to the complementary design of the opening 22 in the humerus plate 20, the sleeve 12 can be aligned comfortably by the surgeon prior to the fixing by corresponding pivoting of the sliding screw. To facilitate the alignment, the bone screw 14 can be cannulated, i.e. can have a throughgoing longitudinal channel, through which a guide wire can be guided with which the sliding screw can be brought into the desired position.

An abutment for the bone screw 14 is formed by its threaded section 16, whereby too deep a sliding into the sleeve 12 is prevented. In addition, the length of the sliding section 18 is dimensioned such that it does not project out on the other side of the sleeve 12 on abutment of the threaded section 16 at the sleeve 12.

To enable the screwing of the headless bone screws 14 into the bone, a passage channel 38 through the head section 26 and for a tool (not shown) for the screwing in of the bone screw 14 is provided, on the one hand, and the end of the threadless sliding section 18 of each bone screw 14 is provided with a slit 34 (see FIG. 6), on the other hand. It is also possible to provide other apparatus instead of a slit for the screwing in of the bone screw 14, for example a hexagon socket. After alignment of the sleeve 12 and the bone screw 14, a tool such as a screwdriver can be passed through the passage channel 38 and its tip engages into the slit 34 and enables a screwing of the threaded section 16 of the bone screw 14 into the bone. A hexagon socket 36 is furthermore provided in the head section 26 of the sleeve 12 and a corresponding tool (not shown) can engage into it to facilitate the alignment of the sleeve 12 and also an at least partial introduction of the sleeve 12 into a bore in the bone.

Figure 4:
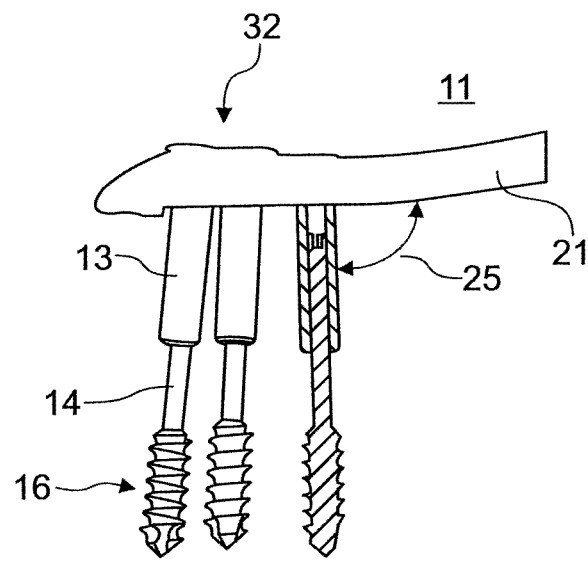
FIG. 4 as a further embodiment of a bone fixing apparatus, a humerus plate with three unidirectionally alignable anchorage elements.
Figure 5:
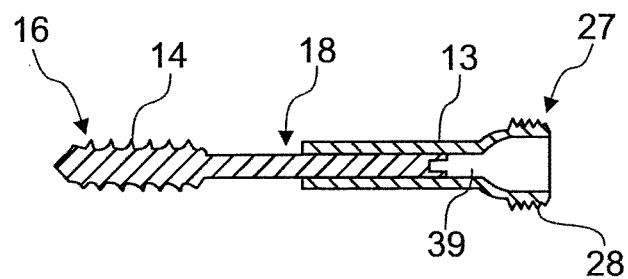
FIG. 5 one of the anchorage elements inserted into the humerus plate of FIG. 4 in a longitudinal section.
Figure 7:
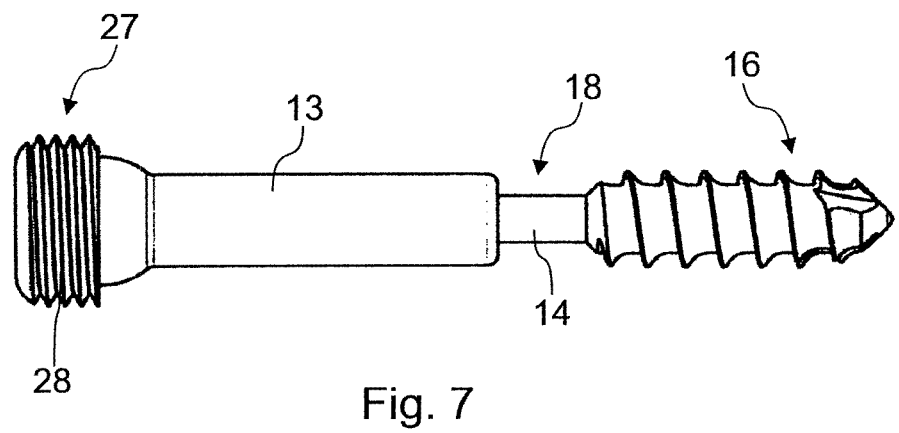
FIG. 7 a design drawing of a unidirectionally alignable anchorage element for a humerus plate.
Figure 8:
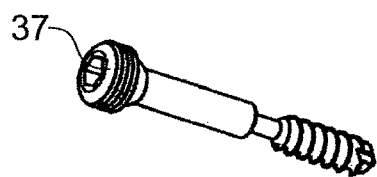
FIG. 8 the anchorage element shown in FIG. 7 in a perspective representation.

FIG. 4 shows a bone fixing apparatus 11 having sleeves 13 unidirectionally fixed in a humerus plate 21. Each head section 27 of a sleeve 13 has an external thread 28 (FIGS. 5, 7, 8) which can be screwed into a corresponding internal thread (not shown in FIG. 4) of an opening 22 of the humerus plate 21 or of a recess 66 of the opening 22 for the reception and support of the sleeve 13. Each bone screw 14 and sleeve 13 (sliding screw) thereby has a preset angle 25 to the humerus plate 21. A variation of the angle 25 is not provided. FIG. 5 shows the sleeve 13 and the bone screw 14 slidingly guided therein in a longitudinal section. FIG. 7 shows the combination of sleeve 13 and screw 14 in a design drawing in a side view and FIG. 8 shows the combination in a perspective view. It can in particular be recognized in FIG. 8 that the head section 27 of the sleeve has a hexagon socket 37 into which a corresponding tool (not shown) for screwing the head screw 27 into an opening 22 in the humerus plate 21 can engage.

Figure 15:
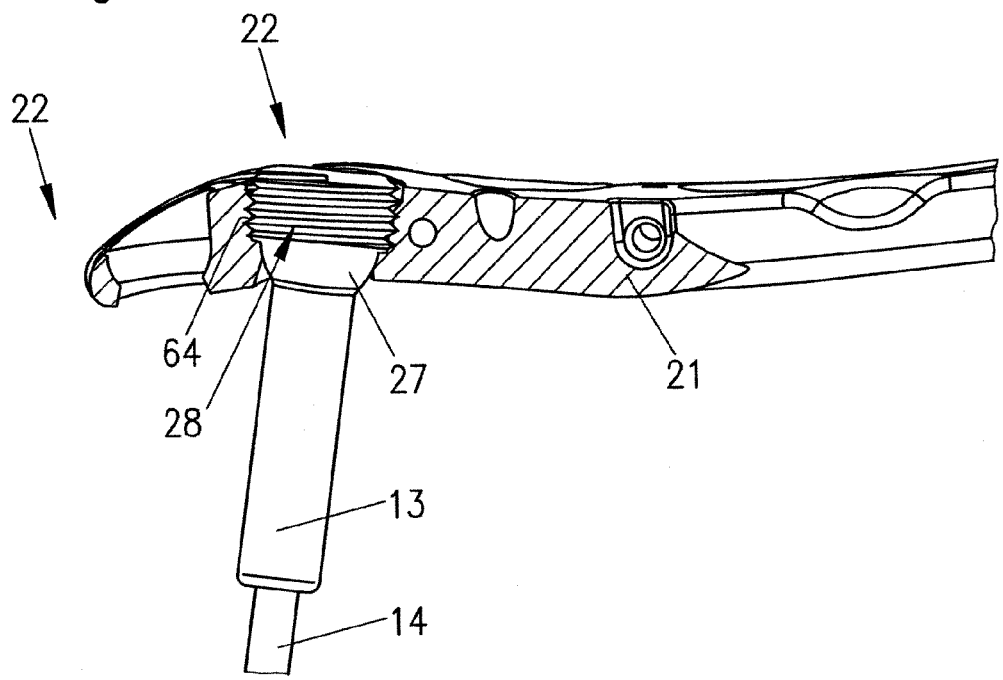
FIG. 15 an embodiment of a unidirectionally alignable anchorage element with a head with an external thread.

FIG. 15 shows an embodiment of a bone fixing apparatus which substantially corresponds to the embodiment shown in FIG. 4, with an external thread 28 of a head 27 of a sleeve 13 engaging into an internal thread 64 of an opening 22 of a bone fixing plate 21 to fix the head 27 unidirectionally at the plate 21.

It is, however, generally also possible both with a polyaxial fixing and a unidirectional fixing that no recess is provided and/or an opening has an internal thread for a closure screw or a siding screw head. Such an opening can in particular also have a throughgoing internal thread.

Provision can generally also be made that a threaded section of the sliding screw which is designed for the anchorage of the sliding screw in the bone has to be screwed through the opening for the conducting of a sliding screw through an opening in a fracture fixing plate having an internal thread. In this case, the outer diameter of the threaded section of the sliding screw is larger than the smallest internal diameter of the opening of the fracture fixing plate and the core diameter of the threaded section of the sliding screw is smaller than the smallest interior diameter of the opening.

It will be described in the following how the bone fixing apparatus shown in FIG. 1 can be surgically implanted. The humerus plate 20 can be introduced into the body in an open manner, i.e. by means of a presentation of the fracture, or minimally invasively using a specific target device (not shown).

After introduction of the plate 20, the fracture of the humerus is reduced using the introduced plate 20 as a pattern for a target unit. The target hoop of the target unit is made as a two-part instrument. The reposition of the fracture is subsequently controlled by X-ray.

To be able to fix the plate 20 at a preset spacing from the bone surface with a stable angle, spacers can be introduced through the openings 22 of the humerus plate 20 between the plate 20 and the bone surface. The spacers are removed again after the final positioning and fixing of the plate 20.

A predrilling into the bone now takes place. The outer diameter is drilled open in accordance with the length of the sleeves 12. Following this, the core diameter of the sliding screw, i.e. of the bone screw 14, is drilled open. This procedure can be carried out under X-ray illumination for better control.

Subsequently, the sliding screws are inserted into the bores in the bone through the corresponding openings 22 of the humerus plate 20 and the bone screws 14 are screwed into the bone. With the polyaxial plate 20, the angular positions of the sliding screws are now fixed using clamping screws 30. With the unidirectional plate 21, the fixing of the sleeves 13 takes place by screwing the sleeves 13 into the plate 21.

Figure 9:
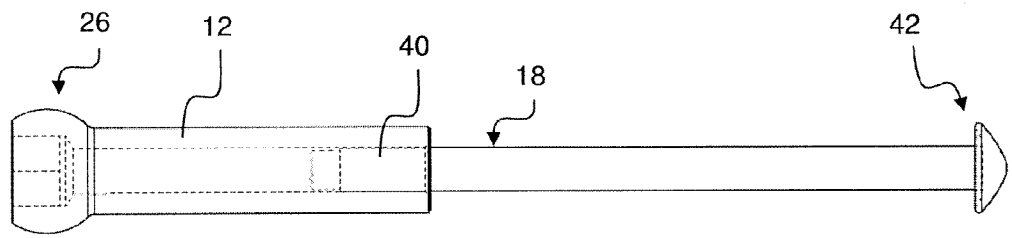
FIG. 9 an embodiment of an anchorage element in which a conical or frustoconical anchorage element is arranged at the tip of a pin-shaped element.

FIG. 9 shows a further embodiment of a sliding anchorage polyaxially fixable in a humerus plate 20 and including a sleeve 12 for the polyaxial fixing of the sliding anchorage in the humerus plate 20 and a pin-shaped element or fastening element slidingly supported therein in the form of a sliding pin 40 which has a conical or frustoconical anchorage section 42, which has no thread, at its tip for the anchorage in the bone.

Figure 10:
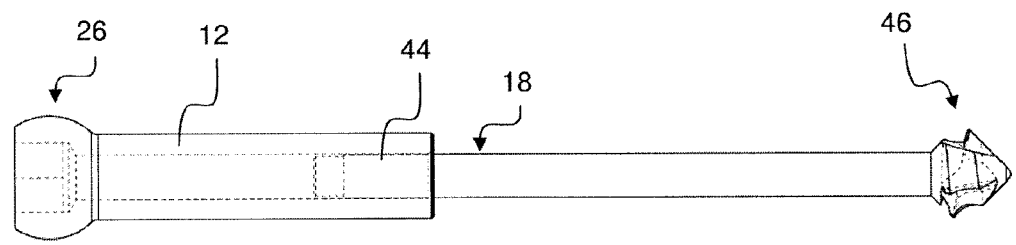
FIG. 10 an embodiment of an anchorage element in which a short threaded section is arranged at the tip of a pin-shaped element for the anchorage in the bone.

A similar embodiment of a sliding anchorage is shown in FIG. 10. In this embodiment, a sliding pin 44 likewise has a conical or frustoconical anchorage section 46 at its tip which, unlike the embodiment shown in FIG. 9, however, has a thread (a so-called threaded ball), which can facilitate the introduction of the sliding pin 44 into the spongiosa somewhat. In the embodiment shown, the thread only has one pitch and even only half a pitch and can therefore be anchored in the bone with a few turns.

Figure 11:
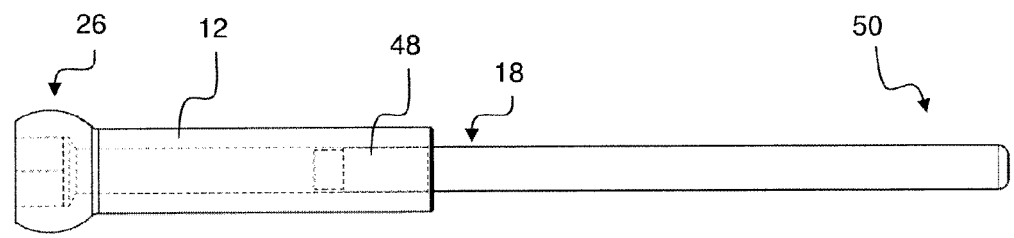
FIG. 11 an embodiment of an anchorage element in which a pin-shaped element is slidingly supported in a sleeve in the form of a sliding pin, a head section of said sleeve being able to be fixed at a stable angle in a humerus plate.

An embodiment of a sliding anchorage is furthermore shown in FIG. 11 which differs from the embodiments shown in FIGS. 9 and 10 in that a sliding pin 48 has a threadless anchorage section 50 and is therefore implemented as a kind of bolt. In principle, the sliding section 18 in this sliding pin 48 merges directly into the threadless anchorage section 50. This sliding pin 48 can therefore be introduced relatively easily into a bore in the bone, in particular by insertion into a predrilled hole in the bone.

Figure 12:
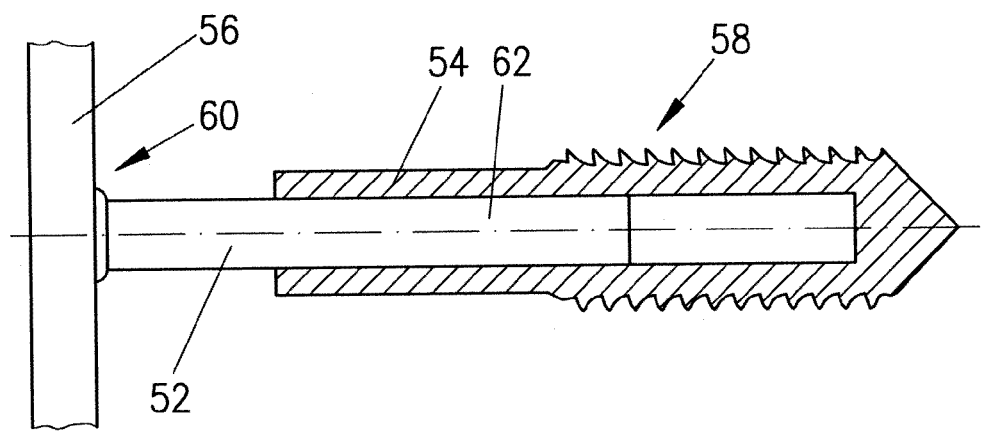
FIG. 12 an embodiment of an anchorage element with a sleeve which is anchored in the bone, which has an external thread and in which a sliding pin is slidingly supported whose head section can be anchored at a stable angle in a humerus plate.

Finally, FIG. 12 shows an embodiment of a sliding anchorage which is shown in section and which includes a sliding pin 52 with a sliding section 62 which is supported in a humerus plate 56 at one end and in a sleeve 54 at the other end which has an external thread 58 for screwing into a bone. The sliding pin 52 can be polyaxially fixed in the humerus plate 56, for example in the manner of FIG. 13 or FIG. 14, and is slidingly supported in the sleeve 54 which is in turn screwed into the bone and is thereby anchored therein. The advantage of such an embodiment of the sliding anchorage is the large achievable polyaxiality since the diameter of the sliding pin 52 can be designed substantially smaller than the opening 22 in the humerus plate 56 in which a head 60 of the sliding pin 52 is supported which is only recognizable sectionally, with the head 60 being designed spherically at the end facing the sliding pin 52. This also allows the setting of very small angles between the humerus plate 56 and the sliding pin 52. The sliding pin can, however, also be fixed unidirectionally in the humerus plate 56, for example in the manner of FIG. 15.

With a surgical implantation, the sleeve 54 can furthermore first be introduced into a bone or a bone fragment at a suitable position. The sleeve 54 in this case does not have to be able to be passed through the opening 22 in the humerus plate 56. A good anchorage can also be ensured in a bone with lower quality by the sleeve 54 which has a comparatively large cross-section relative to the sliding pin 52. The humerus plate 56 can then, optionally with the sliding pin 52 supported therein, be attached outwardly to the bone and can be fixed by the at least partial introduction of the sliding pin 52 into the sleeve 54 anchored in the bone. The sliding pin 52 can furthermore be fixed in the humerus plate 56 with a stable angle to achieve an ideal reduction of a fracture with a simultaneous compressive effect.

Provision can naturally also be made that the sleeve and the opening are dimensioned so that the sleeve can be passed through the opening and the total shaft of the anchorage element can therefore in turn be passed through the opening.

In view of the statements made here, further embodiments of the invention characterized in the claims become clear to the person skilled in the art which cannot be shown conclusively here.

REFERENCE NUMERAL LIST 10 polyaxial bone fixing apparatus
11 unidirectional bone fixing apparatus
12 sleeve for polyaxial fixing in the humerus plate 20
13 sleeve for unidirectional fixing in the humerus plate 21
14 bone screw
16 threaded section
18 sliding section
20 humerus plate with polyaxial fixing of sliding screws
21 humerus plate with unidirectional fixing of sliding screws
22 opening for the support and fixing of the sleeve
24 angle between sleeve 12 and humerus plate 20
25 angle between sleeve 13 and humerus plate 21
26 head section of the sleeve 12
27 head section of the sleeve 13
28 external thread of the head section 27
30 closure screw for the fixing of the sleeve 12
32 section of the humerus plate 20 and 21 provided for the care of the fracture region close to the joint
34 slit for screwing in the bone screw 14
36 hexagon socket of the head section 26 of the sleeve 12
37 hexagon socket of the head section 27 of the sleeve 13
38 passage channel through the head section 26 of the sleeve 12
39 passage channel through the head section 27 of the sleeve 13
40 pin-shaped element
42 (frusto)conical anchorage section
44 pin-shaped element
46 (frusto)conical anchorage section with thread
48 pin-shaped element
50 threadless anchorage section
52 sliding pin
54 sleeve
56 humerus plate
58 external thread of the sleeve 54
60 head of the sliding pin 52
62 sliding section of the sliding pin 52
64 internal thread of the opening 22
66 recess of the opening 22

The invention claimed is:

1. A bone fixing apparatus for the surgical care of fractures, including:
    a fracture fixing plate which has a first side configured to face a bone, a second side configured to face away from the bone, and at least one opening, wherein the fracture fixing plate has a recess in a region of the opening; and
    at least one anchorage element for fastening the fracture fixing plate to a bone, the anchorage element including a shaft and a head,
    wherein at least a part of the shaft is configured to pass through the opening, whereas the head is completely received in the recess on the second side of the fracture fixing plate such that the head is beneath the second side of the fracture fixing plate, the head configured to fix in the opening, and the shaft including at least a first part at which the head is arranged and a second part configured to anchor in the bone, the first part including a sleeve and the second part including a sliding section and a threaded section, the first part and the second part guided displaceably with respect to one another along a longitudinal axis when the bone fixing apparatus is fixed to the bone, wherein the sleeve receives the sliding section and the threaded section such that a portion of the sliding section and the threaded section extend from the sleeve and slide in a linear manner along the longitudinal axis, wherein the threaded section is configured to engage with the bone.

2. The bone fixing apparatus of claim 1, wherein the sleeve includes an inner guide region and a pin-shaped element received therein and includes an outer guide region, said inner and outer guide regions each having a constant cross-section in the direction of the axis such that the outer guide region can slide in a linearly guided manner in the direction of the longitudinal axis in the inner guide region.

3. The bone fixing apparatus of claim 2, wherein the pin-shaped element is configured to anchor in the bone and the sleeve is configured to fix in the at least one opening of the fracture fixing plate.

4. The bone fixing apparatus of claim 2, wherein said inner and outer guide regions each have a constant circular cross-section in the direction of the axis.

5. The bone fixing apparatus of claim 1, wherein an angular position of the anchorage element relative to the plate is adjustable within a preset range before the bone fixing apparatus is fixed to the bone.

6. The bone fixing apparatus of claim 1, wherein means are provided to connect the head of the anchorage element to the plate.

7. The bone fixing apparatus of claim 1, wherein the opening is sized to at least partially receive the head of the anchorage element.

8. The bone fixing apparatus of claim 1, further including a blocking element configured to block the head within at least one of the opening and a recess of the opening.

9. The bone fixing apparatus of claim 8, wherein at least one of the opening and the recess has an internal thread, the blocking element having an external thread for the blocking of the head by screwing into the internal thread.

10. The bone fixing apparatus of claim 9, wherein the blocking element is in the shape of one of a closure ring and a closure screw.

11. The bone fixing apparatus of claim 1, wherein:

the plate has a concave support surface in a region of at least one of the opening and a recess of the opening facing a side of the plate facing the bone; and the head is designed spherically at an end facing the shaft such that an angular position of the anchorage element relative to the plate is variable before the bone fixing apparatus is fixed to the bone.

12. The bone fixing apparatus of claim 1, wherein the fracture fixing plate is configured to be substantially fixed to the bone without contacting a surface of the bone.

13. The bone fixing apparatus of claim 1, wherein the fracture fixing plate is configured for use in at least one of an epiphyseal region and a metaphyseal region of a bone.

14. The bone fixing apparatus of claim 13, wherein the fracture fixing plate is configured for use on a proximal humerus.

15. The bone fixing apparatus of claim 1, wherein the head and the opening are sized to prevent the head from passing through the opening.

16. The bone fixing apparatus of claim 15, wherein the shaft of the anchorage element is sized to pass entirely through the opening.

* * * * *

UNITED STATES PATENT AND TRADEMARK OFFICE
CERTIFICATE OF CORRECTION

PATENT NO.        : 8,641,740 B2                                            Page 1 of 1
APPLICATION NO. : 12/680120
DATED             : February 4, 2014
INVENTOR(S)       : Kuster et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 341 days.

Signed and Sealed this
Twenty-second Day of September, 2015

Michelle K. Lee
*Director of the United States Patent and Trademark Office*